(12) United States Patent
Nzike et al.

(10) Patent No.: US 10,518,027 B2
(45) Date of Patent: Dec. 31, 2019

(54) PERISTALTIC PUMP

(71) Applicant: SANOFI-AVENTIS DEUTSCHLAND GMBH, Frankfurt am Main (DE)

(72) Inventors: Philippe Nzike, Frankfurt am Main (DE); Michael Schabbach, Frankfurt am Main (DE); Olaf Zeckai, Weinheim (DE); Meinolf Werner, Worms (DE); Ole Simonowsky, Blankenrath (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 131 days.

(21) Appl. No.: 15/387,065

(22) Filed: Dec. 21, 2016

(65) Prior Publication Data

US 2017/0157320 A1    Jun. 8, 2017

Related U.S. Application Data

(63) Continuation of application No. 14/240,797, filed as application No. PCT/EP2012/068695 on Sep. 21, 2012, now Pat. No. 9,586,002.

(30) Foreign Application Priority Data

Sep. 21, 2011  (EP) .................... 11182228

(51) Int. Cl.
*A61M 5/142* (2006.01)
*F04B 43/12* (2006.01)
*A61M 5/158* (2006.01)
*F04B 43/00* (2006.01)

(52) U.S. Cl.
CPC ........ *A61M 5/14228* (2013.01); *A61M 5/158* (2013.01); *F04B 43/0072* (2013.01); *F04B 43/1253* (2013.01); *F04B 43/1284* (2013.01)

(58) Field of Classification Search
CPC .. F04B 43/1253; F04B 43/12; F04B 43/1223; A61M 5/14228; A61M 5/14232
See application file for complete search history.

(56) References Cited

U.S. PATENT DOCUMENTS

| 533,575 | A | 2/1895 | Wilkens |
| 3,116,697 | A | 1/1964 | Bilichniansky |
| 5,226,895 | A | 7/1993 | Harris |
| 5,279,586 | A | 1/1994 | Balkwill |
| 5,304,152 | A | 4/1994 | Sams |

(Continued)

FOREIGN PATENT DOCUMENTS

| CH | 417338 A | 7/1966 |
| DE | 19729612 | 1/1999 |

(Continued)

OTHER PUBLICATIONS

European Examination Report for EP Application No. 12759778.9, dated Jul. 19, 2016.

(Continued)

*Primary Examiner* — Emily L Schmidt
(74) *Attorney, Agent, or Firm* — McCarter & English, LLP

(57) ABSTRACT

A peristaltic pump comprises a tube for transporting a material, wherein the tube is arranged linearly along a longitudinal axis. The peristaltic pump further comprises a pump head for causing a squeezing of the tube, wherein the pump head is rotatable about a rotation axis.

21 Claims, 5 Drawing Sheets
Specification includes a Sequence Listing.

(56) References Cited

U.S. PATENT DOCUMENTS

| | | |
|---|---|---|
| 5,320,609 A | 6/1994 | Haber et al. |
| 5,383,865 A | 1/1995 | Michel |
| 5,480,387 A | 1/1996 | Gabriel et al. |
| 5,505,704 A | 4/1996 | Pawelka et al. |
| 5,582,598 A | 12/1996 | Chanoch |
| 5,626,566 A | 5/1997 | Petersen et al. |
| 5,674,204 A | 10/1997 | Chanoch |
| 5,688,251 A | 11/1997 | Chanoch |
| 5,921,966 A | 7/1999 | Bendek et al. |
| 5,961,495 A | 10/1999 | Walters et al. |
| 6,004,297 A | 12/1999 | Steenfeldt-Jensen et al. |
| 6,193,698 B1 | 2/2001 | Kirchhofer et al. |
| 6,221,046 B1 | 4/2001 | Burroughs et al. |
| 6,235,004 B1 | 5/2001 | Steenfeldt-Jensen et al. |
| 6,248,095 B1 | 6/2001 | Giambattista et al. |
| 6,899,698 B2 | 5/2005 | Sams |
| 6,936,032 B1 | 8/2005 | Bush, Jr. et al. |
| 7,241,278 B2 | 7/2007 | Moller |
| 2002/0052578 A1 | 5/2002 | Moller |
| 2002/0120235 A1 | 8/2002 | Enggaard |
| 2003/0050609 A1 | 3/2003 | Sams |
| 2004/0059299 A1 | 3/2004 | Moller |
| 2004/0210199 A1 | 10/2004 | Atterbury et al. |
| 2004/0267207 A1 | 12/2004 | Veasey et al. |
| 2005/0054971 A1 | 3/2005 | Steen et al. |
| 2005/0113765 A1 | 5/2005 | Veasey et al. |
| 2006/0153693 A1 | 7/2006 | Fiechter et al. |
| 2007/0212240 A1 | 9/2007 | Voyeux et al. |
| 2009/0275916 A1 | 11/2009 | Harms et al. |
| 2011/0004161 A1* | 1/2011 | Ito .................... A61M 5/14232 604/154 |
| 2014/0212314 A1 | 7/2014 | Baron |

FOREIGN PATENT DOCUMENTS

| | | | |
|---|---|---|---|
| DE | 10246469 | 4/2004 | |
| EP | 0937471 | 8/1999 | |
| EP | 0937476 | 8/1999 | |
| EP | 1612423 | 1/2006 | |
| GB | 979330 A | 1/1965 | |
| JP | H09-222084 A | 8/1997 | |
| JP | 2001-526916 A | 12/2001 | |
| WO | 99/22783 A1 | 5/1999 | |
| WO | 99/38554 | 8/1999 | |
| WO | 01/10484 | 2/2001 | |
| WO | WO2009107737 | * 9/2009 | ........ A61M 5/14232 |

OTHER PUBLICATIONS

Japanese Office Action for JP Application No. 2014-531252, dated Jul. 5, 2016.

International Search Report for Int. App. No. PCT/EP2012/068695, completed Nov. 19, 2012.

* cited by examiner

PERISTALTIC PUMP

CROSS REFERENCE TO RELATED APPLICATIONS

The present application is a continuation of U.S. patent application Ser. No. 14/240,797, filed Feb. 25, 2014, which is a U.S. National Phase Application pursuant to 35 U.S.C. § 371 of International application Ser. No. PCT/EP2012/068695 filed Sep. 21, 2012, which claims priority to European Patent Application No. 11182228.4 filed Sep. 21, 2011. The entire disclosure contents of these applications are herewith incorporated by reference into the present application.

TECHNICAL FIELD

The present disclosure relates to a peristaltic pump. Peristaltic pumps are configured to transport a material in a tube by squeezing the tube.

BACKGROUND

Peristaltic pumps are known, for example, from the documents DE 10246469 A1 and DE 19729612 A1.

SUMMARY

One object of the present invention is to provide a peristaltic pump with improved properties.

According to one aspect of the present disclosure, a peristaltic pump comprises a tube for transporting a material, wherein the tube is arranged along a longitudinal axis. The peristaltic pump further comprises a rotatable pump head for causing a squeezing of the tube. The pump head may be rotatable about a rotation axis.

The peristaltic pump may be configured to be applied for medical use. Preferably, the peristaltic pump is configured to transport a medicament, for example a fluid medicament. In particular, the pump may be used in the field of micro fluidics. As an example, the peristaltic pump may be configured to dispense small amounts of fluids. The pump may be used for a transporting a highly sensitive material. The material to be transported may be a medicament, for example insulin. Accordingly, the peristaltic pump me be used as a drug delivery device.

The peristaltic pump may comprise a receptacle. The receptacle may be configured to receive a cartridge or container holding the material to be transported.

Due to the arrangement of the tube along a longitudinal axis, an exchange of the tube may become easy and reproducible, since the handling and positioning of the tube may be facilitated. Thereby, the risk of misalignment of the tube, for example relative to the pump head, may be reduced. This may lead to a higher dosing accuracy after an exchange of the tube.

Preferably, the tube is arranged along the longitudinal axis at least in a section of the tube which is configured to be squeezed for transporting the material. Preferably, the tube is arranged along the longitudinal axis along its entire length. Preferably, the tube is free of curved sections. In particular, the tube may be free of U-shaped sections.

Preferably, the pump is configured such that the material is transported in a transport direction. Preferably, the transport direction is parallel to the longitudinal axis.

Preferably, the pump head causes a squeezing of the tube along the longitudinal axis of the tube, in particular along the transport direction. Thereby, a transport of the material in the transport direction may be caused. In particular, the pump head may be configured such that a squeezed patch of the tube moves along the longitudinal axis. This may lead to an overpressure in the tube in front of the squeezed patch, which may lead to a movement of the material in the transport direction.

Preferably, the rotation axis of the pump head is perpendicular to the longitudinal axis.

In this case, a compact size of the peristaltic pump may be achieved, because the pump head may have a small dimension in direction of the longitudinal axis.

The pump head may comprise a least one squeeze member for squeezing the tube.

In particular, the squeeze member may be configured to be in mechanical contact with the tube for squeezing the tube. Preferably, the squeeze member may be configured to close the tube at least at a particular time when squeezing the tube. In a preferred embodiment, the squeeze member squeezes the tube in a section of the tube running along the longitudinal axis. The section may run from a first position at the tube to a second position at the tube. Preferably, the squeeze member squeezes the tube continuously from the first position to the second position and thereby moves the squeezed patch from the first position to the second position.

In a preferred embodiment, the peristaltic pump is configured such that the squeeze member is enabled to roll off on the tube when squeezing the tube.

In this way, friction forces may be kept small. Thereby, an axial deformation of the tube or a displacement of the tube in axial direction may be prevented. Furthermore, a low driving force for driving the pump head may be sufficient such that the driving motor can be kept small. In particular, the friction force between the squeeze member and the tube may be a rolling friction force, which is smaller than a sliding friction force. As an example, the squeeze member may comprise a spherical or cylindrical member, for example a ball or a roller.

Preferably, the pump head is configured to be operated at a constant driving speed. Thereby, a constant, nearly shock free pumping may be achieved with a low variation of a pumping pressure. Furthermore, a high dosing accuracy may be achieved.

The pump head may comprise a support member for supporting the squeeze member. Preferably, by a rotation of the pump head also the support member rotates, in particular rotates about the rotation axis of the pump head.

In a preferred embodiment, the squeeze member is supported by the support member such that a rotation of the squeeze member relative to the support member is enabled.

In particular, the squeeze member may be rotatable relative to the support member about a further rotation axis, arranged in a distance from the rotation axis of the pump head. The further rotation axis may run through the center of the squeeze member. The further rotation axis may be parallel to the rotation axis of the pump head. Preferably, the squeeze member is rotatable both about the rotation axis of the pump head and about the further rotation axis.

The support member may comprise a disk-like shape. The squeeze member may be located near an outer perimeter of the support member. The squeeze member may be supported on the support member by a shaft. The shaft may run through the squeeze member. The shaft may be in direct contact with the support member. In one embodiment, the support member comprises two parts. Each of the parts may support an end of the shaft. The squeeze member may be located between the two parts of the support member.

In a preferred embodiment, the pump is configured such that the squeeze member is shiftable in a radial direction relative to the rotation axis.

Thereby, an adjustment of the radial position of the squeeze member relative to the rotation axis may be enabled. In particular, the distance of the squeeze member to the rotation axis of the pump head may be adjustable.

The squeeze member may be supported by a support member such that a movement in a radial direction is enabled. As an example, the support member may comprise a slot for supporting the squeeze member. The squeeze member may be shiftable in the slot. In particular, the squeeze member may be supported by a shaft being guided in the slot. Preferably, the slot extends in radial direction such that a movement of the squeeze member in radial direction is enabled.

In a preferred embodiment, the pump is configured such that a movement of the squeeze member along the longitudinal axis of the tube is enabled. Preferably, a movement along the longitudinal axis may be enabled at least along a section of the tube. In particular, the squeeze member may carry out a linear movement along the tube.

Thereby, the squeeze member may squeeze the tube and move the squeezed patch of the tube along the longitudinal axis. Preferably, the squeeze member squeezes the tube at the squeezed patch such that the tube is closed in the squeezed patch in a section running along the longitudinal axis. Thereby, a reflow of material can be prevented.

In a preferred embodiment, the peristaltic pump comprises a guide member for guiding a movement of the squeeze member.

In particular, the guide member may confine a movement of the squeeze member in a radial direction relative to the rotation axis of the pump head. In particular, the guide member may confine a movement in the radial direction towards the rotation axis.

Preferably, the guide member is secured to a housing of the pump such that relative movements between the guide member and the housing are prevented. In particular, the guide member may be non-rotatable.

The squeeze member may be supported by a shaft, wherein a movement of the shaft in radial direction may be confined by a mechanical stop of the guide member. In particular, when the shaft abuts the guide member, a movement of the shaft in a radial direction, in particular towards the rotation axis of the pump head, may be prevented.

The guide member may be configured to guide a movement of the squeeze member along the longitudinal axis.

In particular, the guide member may guide the squeeze member in an axial movement of the squeeze member, preferably in a section of the tube which is configured to be squeezed by the squeeze member. In particular, during the axial movement of the squeeze member the squeeze member may squeeze the tube and thereby displace a squeezed patch of the tube in axial direction.

The peristaltic pump may further comprise a tube guide for guiding the tube.

In particular, the tube may be located on the tube guide. The tube guide may serve to position the tube in the pump. The tube may be attached to the tube guide. As an example, the tube guide may comprise a longitudinal grove in which the tube runs. The tube may be positioned between the tube guide and the pump head.

The guide member may cooperate with the tube guide to cause a movement of the squeeze member along the longitudinal axis. In particular, the guide member may be arranged such relative to the tube guide that the radial position of the squeeze member is confined in one radial direction by the guide member and in the opposite radial direction by the tube guide. Preferably, along a section of the tube, the radial position of the squeeze member is determined by the guide member and the tube guide.

Preferably, the axial movement of the squeeze member is enabled by a shiftability of the squeeze member as described above. Thereby, during rotation of the pump head the radial position of the squeeze member may be adjusted such that an axial movement of the squeeze member results.

In a preferred embodiment, a perimeter of the guide member comprises a linear section extending parallel to the longitudinal axis of the tube.

In particular, the squeeze member may be guided along the linear section when moving in an axial direction and squeezing the tube. As an example, a shaft for supporting the squeeze member may run along the perimeter of the guide member. When the shaft runs along the linear section, in particular abuts the linear section, the squeeze member may be guided in an axial movement.

Furthermore, the perimeter of the guide member may comprise a curved section.

The squeeze member may run along the curved section when not squeezing the tube. In particular, the squeeze member may be transported back from a second position at the tube to a first position at the tube when running along the curved section. Preferably, the curved section delimits a radial movement of the squeeze member towards the rotation axis. However, a radial movement of the squeeze member in the opposite radial direction may be allowed.

The peristaltic pump may comprise a plurality of squeeze members.

Preferably, the squeeze members are arranged on a support member of the pump head. In particular, the squeeze members may be arranged near an outer perimeter of the support member. In particular, the squeeze members may be arranged at regular distances from each other.

Preferably, at any time during an operation of the pump, at least one of the squeeze members squeezes the pump, in particular such that the pump is closed. Thereby, a reflow of the material in a direction opposite to the transport direction may be prevented. Accordingly, the squeeze members may serve as valves.

In a preferred embodiment, the peristaltic pump comprises a main part and an exchange part. The exchange part may be configured to the detachable from the main part.

The exchange part may be configured to carry elements of the peristaltic pump which have to be exchanged periodically. As an example, the exchange part may carry the tube or a needle. Preferably, the elements which are carried by the exchange part are pre-assembled at the exchange part. This may allow an easy and quick exchange of parts of the pump. The exchange part may be configured to be disposable such that the exchange part may be replaced by a new exchange part. In a further embodiment, the exchange part may be configured such that a separate exchange of individual elements, such as a needle or the tube, may be enabled.

Preferably, the exchange part comprises a tube guide for guiding the tube. The exchange part may comprise the tube.

The main body may comprise the pump head. Furthermore, the main body may comprise a receptacle for receiving a cartridge or container holding the material to be transported.

The peristaltic pump may comprise at least one needle. As an example, the exchange part may be configured to carry at least one needle.

In particular, a needle may be provided for dispensing the material from a dispensing end of the pump. The needle may be in fluid connection with the tube. Additionally or alternatively, the pump may comprise at least one needle by which the tube is provided with new material. In particular, the needle may be configured to be inserted into a cartridge or container such that the material can flow from the cartridge or container into the tube.

The term "medicament", as used herein, preferably means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group-Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2) 25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2) 25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

BRIEF DESCRIPTION OF THE FIGURES

Further features, refinements and expediencies become apparent from the following description of the exemplary embodiments in connection with the figures.

Like elements, elements of the same kind and identically acting elements may be provided with the same reference numerals in the figures.

DETAILED DESCRIPTION

Figure 1:
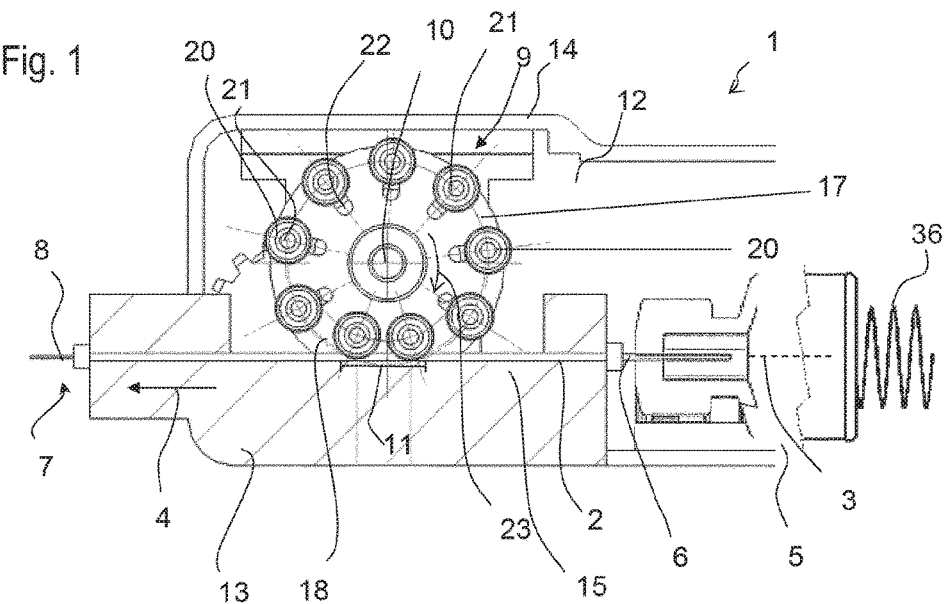
FIG. 1 shows a sectional side view of a peristaltic pump.

FIG. 1 shows a sectional side view of an embodiment of a peristaltic pump 1. The pump 1 comprises a linear tube 2 extending along a longitudinal axis 3. The tube 2 is free from curved portions. A material is transported through the tube 2 in a transport direction 4. The transport direction 4 is parallel to the longitudinal axis 3.

The material to be transported is held by a cartridge or container 5 positioned in a receptacle, for example a glass cartridge. As an example, the peristaltic pump 1 may be configured to transport and dispense a medical fluid, for example insulin. The peristaltic pump 1 may be particularly suitable for transporting small amounts of a fluid, such that the peristaltic pump 1 may be used in the field of micro fluidics. The cartridge 5 may comprise a piston. The piston may be axially movable in the cartridge 5. A spring 36 may exert a force on the piston to facilitate a movement of the piston. Thereby, air pockets in the receptacle 5 may be prevented when material is drawn from the cartridge 5 into the tube 2. The cartridge 5 may also be made from a different material, for example synthetic material like plastics. The cartridge or container 5 may also be made from a collapsible or flexible material. In this case, a piston is not required.

The peristaltic pump 1 comprises a first needle 6, which is in fluid communication with the cartridge or container 5 and connects the cartridge or container 5 to the tube 2. The first needle 6 may pierce a septum of the cartridge or container 5. At a dispending end 7 of the peristaltic pump 1, a second needle 8 is located. The second needle 8 is in fluid communication with the tube 2. Preferably, the second needle 8 is insertable in a tissue to dispense the material.

The peristaltic pump 1 comprises a main part 12 and an exchange part 13. The exchange part 13 is detachably attached to the main part 12. Thereby, a replacement of the exchange part 13 or of individual components of the exchange part 13 may be enabled. Preferably, the exchange part 13 comprises parts of the peristaltic pump 1 which have to be exchanged periodically, such as the needles 6, 8 and the tube 2.

The main part 12 comprises a housing 14 which houses a pump head 9 and the receptacle for the cartridge and container 5. The exchange part 13 comprises a tube guide 15, wherein the tube 2 is guided. The tube 2 may be detachably attached to the tube guide 15 such that the tube 2 in the exchange part 13 may be individually replaceable. As a further example, the tube 2 may be permanently attached to the exchange part, for example glued to the tube guide 15.

The pump head 9 of the pump 1 is rotatably mounted. The pump head 9 is rotatable about a rotation axis 10 in a rotational direction 23. By a rotation of the pump head 9, a squeezing of the tube 2 along the longitudinal axis 3 is caused such that a squeezed patch of the tube 2 propagates in transport direction 4. In particular, the squeezing of the tube 2 is caused in a section 11 of the tube.

The pump head 9 comprises a support member 17 supporting a plurality of squeeze members 20. In this embodiment, the squeeze members are configured as rollers. The squeeze members 20 are rotatably mounted on the support member 17 such that a relative rotational movement of the squeeze members 20 and the support member 17 is enabled. In particular, each squeeze member 20 is mounted on the support member 17 by a shaft 21 such that the squeeze member 20 is rotatable about a further rotational axis running through the center of the shaft 21. The rotational axis 10 and the further rotational axis are parallel to each other and are perpendicular to the longitudinal axis 3.

When the pump head 9 and thereby also the support member 17 and the squeeze members 20 are rotated about the rotational axis 10, a squeeze member 20 comes into contact with the tube 20, squeezes the tube along at least the section 11 and then leaves the tube 2. The rotatable mounting of the squeeze member 20 on the support member 17 enables the squeeze member 20 to roll off on the tube 2 when squeezing the tube 2. Thereby, friction forces may be kept low and an axial deformation of the tube 2 may be reduced.

The squeeze members 20 are shiftably mounted such that a displacement of the squeeze members 20 in a radial direction relative to the rotation axis 10 is enabled. In particular, the shafts 21 are located in radial slots 22 of the support member 17 such that a displacement of the shafts 21 and, thereby, of the squeeze members 20 in a radial direction is enabled.

Due to this shiftability, the squeeze members 20 are enabled to move linearly along the longitudinal axis 3 when squeezing the tube 2 in the tube section 11. In particular, during a rotation of the pump head 9 about the rotation axis 10, the radial position of the squeeze members 20 relative to the rotation axis 10 can be adjusted such that the squeeze members 20 are urged into a linear movement along the longitudinal axis 3 at least along the section 11 of the tube 2. Thereby, a squeezing of the tube 2 along a linear path is enabled.

In the following, the working principle of the pump of FIG. 1 is described in more detail in connection with FIGS. 2, 3 and 4A to 4G.

Figure 2:
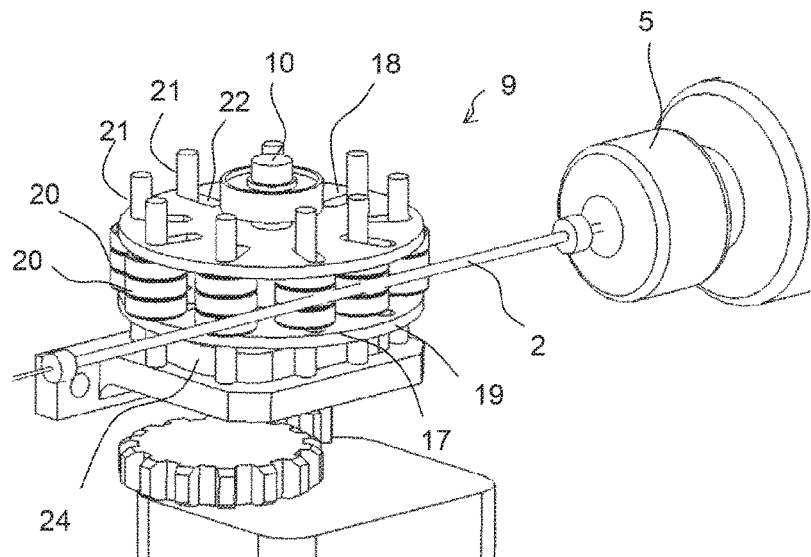
FIG. 2 shows a perspective view of the pump head of the peristaltic pump of FIG. 1.

FIG. 2 shows a perspective view of the pump head 9 in the peristaltic pump 1 of FIG. 1.

The support member 17 comprises two circular discs 18, 19. The squeeze members 20 are located between the circular discs 18, 19. Each of the circular discs 18, 19 comprises a plurality of slots 22, wherein the shafts 21 are shiftably mounted.

In order to urge the squeeze members 20 into a movement along the longitudinal axis 3 in the section 11 of the tube 2, the peristaltic pump 1 comprises a guide member 24.

The shafts 21 of the squeeze members 22 are arranged such that the ends of the shafts 21 run along the outer perimeter of the guide member 24 during a rotation of the pump head 9. Thereby, the radial movement of the squeeze members 22 in a direction towards the rotation axis 10 is confined by the guide member 24. In particular, when a shaft 21 abuts the outer perimeter of the guide member 24, a further movement in a radial direction towards the rotation axis 10 is prevented.

Figure 3:
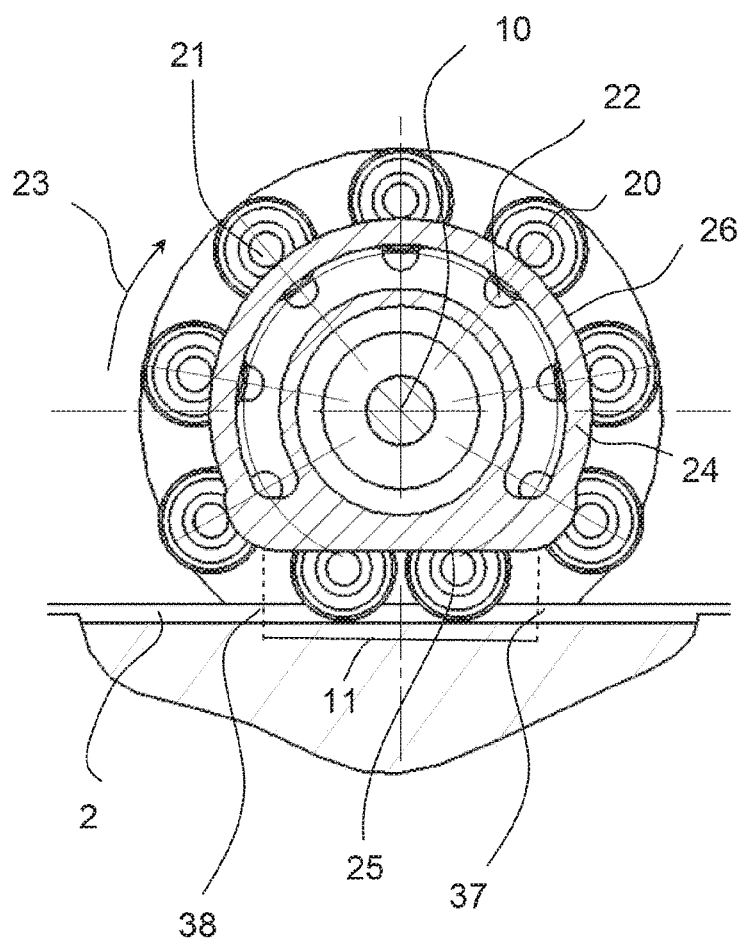
FIG. 3 shows a side view of the pump head of the pump of FIG. 1.

As can be seen in FIG. 3, the perimeter of the guide member 24 comprises a linear section 25, which may also be denoted as the guide rail, and a curved section 26. During operation of the pump 1, each shaft 21 and, thereby, each squeeze member 20 is moved along the perimeter of the guide member 24 in the rotational direction 23. When a squeeze member 20 is guided along the linear section 25, it moves linearly along the longitudinal axis 3. The length of the linear section 25 corresponds to the length of the section 11, in which the squeeze member moves linearly along the tube 2 and, thereby, squeezes the tube 2. The section 11 extends from a first position 37 at the tube 2 towards a second position 38 at the tube 2, which corresponds to a start of the linear section 25 resp. an end of the linear section 25.

FIGS. 4A to 4G show a sectional side view of the pump head 9 during operation of the pump 1. In particular, the movement of a squeeze member 20 along the guide member 24 during a rotation of the pump head 9 is shown. For clarity reasons, only one of the squeeze members 20 is depicted.

Figure 4A:
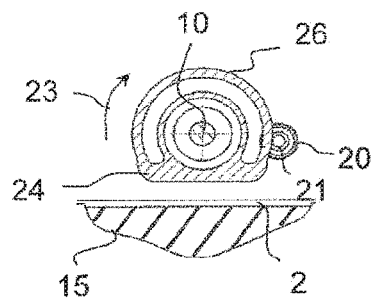
FIGS. 4A to 4G show a sectional side view of the pump head during the operation of the pump of FIG. 1.

In FIG. 4A, the squeeze member 20 is located at the curved section 26 of the guide member 24. In particular, the shaft 21 of the squeeze member 20 may abut the curved section 26 or may be located in a distance from the curved section 26. The shaft 21 may be shiftable in the slot 21 from the curved section 26 in a radial direction away from the rotation axis 10. Thus, when the shaft 21 is guided along the curved section 26, the exact radial position of the shaft 21 may be undefined.

Figure 4B:
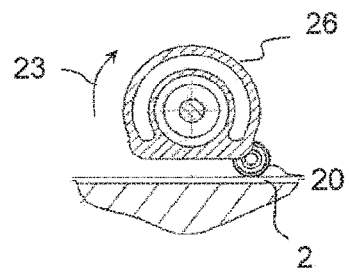

As shown in FIG. 4B, when the pump head 9 and, thereby, the support member 17 and the squeeze member 20 is rotated further in the rotational direction 23, the squeeze member 20 reaches the end of the curved section 26 and gets into contact with the tube 2.

Figure 4C:
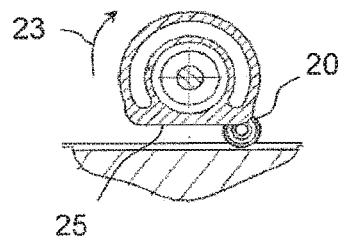

As shown in FIG. 4C, on a further rotation of the pump head 9, the squeeze member 20 enters the linear section 25 of the perimeter of the guide member 24 and arrives at the first position 37 at the section 11 of the tube 2 (see FIG. 3). In the linear section 25 of the guide member 24, the squeeze member 20 is guided by the linear section 25 of the guide member 24 and by the tube guide 15. In particular, the shaft 21 abuts the linear section 25, whereby the radial movement of the squeeze member 20 towards the rotational axis 10 is delimited. In the opposite radial direction, the radial movement of the squeeze member 20 is delimited by the tube guide 25, on which the tube 2 is located. Accordingly, the radial position of the squeeze member 20 is determined by the linear section 25 of the guide member 24 and the tube 2. Because the linear section 25 and the tube guide 2 extend along the longitudinal axis 3, the radial position of the squeeze member 20 is adjusted such that a linear movement of the squeeze member 20 along the longitudinal axis 3 is caused.

Figure 4D:
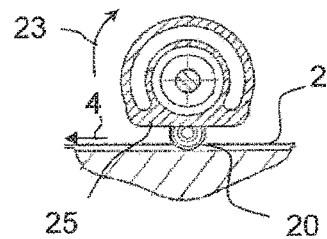

FIG. 4D shows a position of the squeeze member 20 after a further rotation of the pump head 9. The squeeze member 20 has moved along the linear section 11 of the tube 2. Due to the linear movement of the squeeze member 20, a squeezed patch of the tube 2 is moved in the transport direction 4. Thereby, the material in the tube 2 is transported in the transport direction 4. Preferably, all along the linear section 25, the squeeze member 20 squeezes the tube 2 such that the tube 2 is closed. Thereby, a reflow of the material in a direction opposite to the transport direction 4 may be inhibited.

Due to the rotatable mounting of the squeeze member 20 relative to the support member 17 the squeeze member 20 rolls off on the tube 2 when squeezing the tube 2.

Figure 4E:
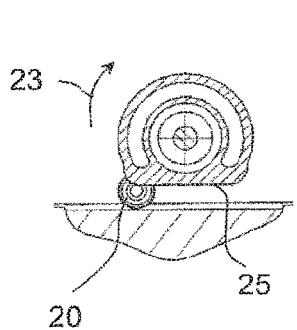

FIG. 4E shows a position of the squeeze member 20 after a further rotation of the pump head 9. The squeeze member 20 has reached the end of the linear section 25.

Figure 4F:
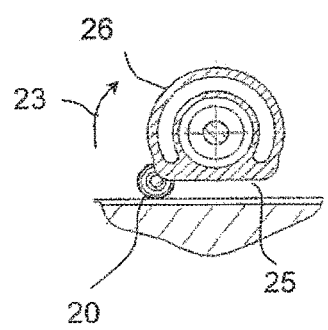

On a further rotation, the squeeze member 20 leaves the linear section 25 and enters the curved section 26 as shown in FIG. 4F. In particular, the shaft 22 gets out of contact with the linear section 25 and is guided along the curved section 26. In this position, the squeeze member 20 is still in contact with the tube 2 but does not close the tube 2.

Figure 4G:
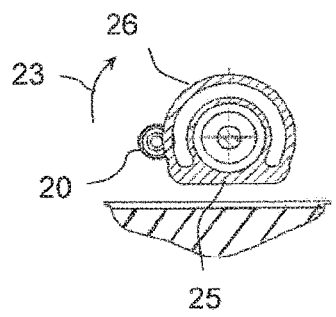

FIG. 4G shows the squeeze member 20 after a further rotation of the pump head 9. In this position, the squeeze member 20 is out of contact from the tube 2. On a further rotation, the squeeze member 20 is transported along the curved section 26 and reaches again the position as shown in FIG. 4A.

Preferably, at any time during operation of the pump 1, at least one squeeze member 20 is in contact with the tube 2. More preferably, at least one squeeze member 20 squeezes the tube 2 such that the tube 2 is closed. Thereby, a reflow of material may be inhibited.

In an alternative embodiment, the squeeze members 20 are pressed by a resilient force towards the outside end of the slots 22 near the outer perimeter of the discs 18 and 19, for example by a spring force. For example, shafts 21 of squeeze members 20 may be suspended by springs that press the shafts against the outside end of the slots 22. In such an embodiment, the guide member 24 is not required, as the squeeze members 20 squeeze the tube 2 by the spring forces.

Figure 5:
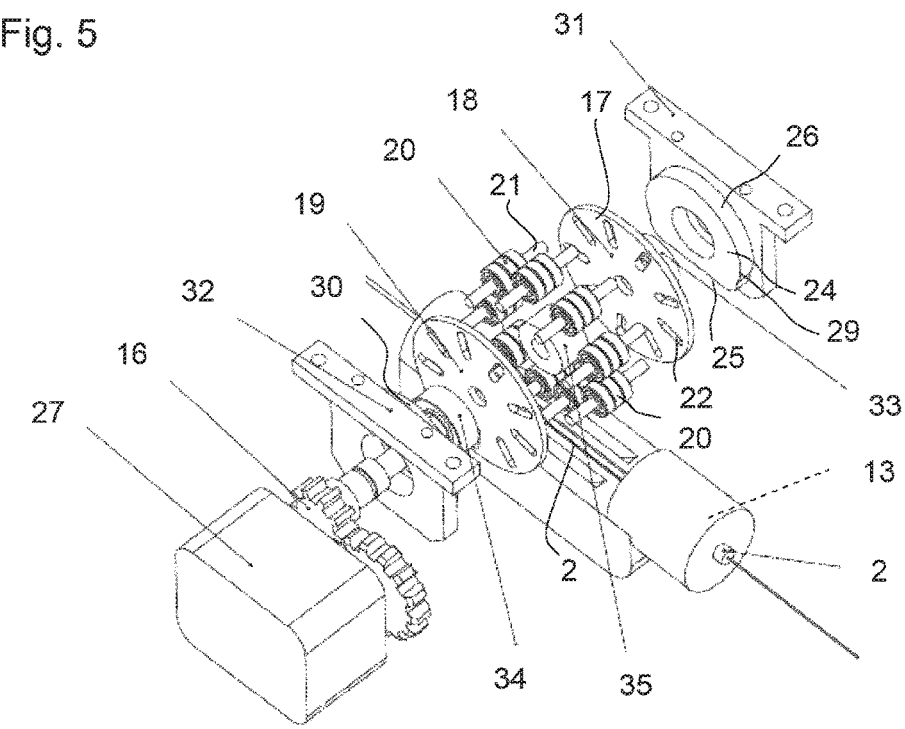
FIG. 5 shows a perspective exploded view of parts of the peristaltic pump of FIG. 1.
Figure 6:
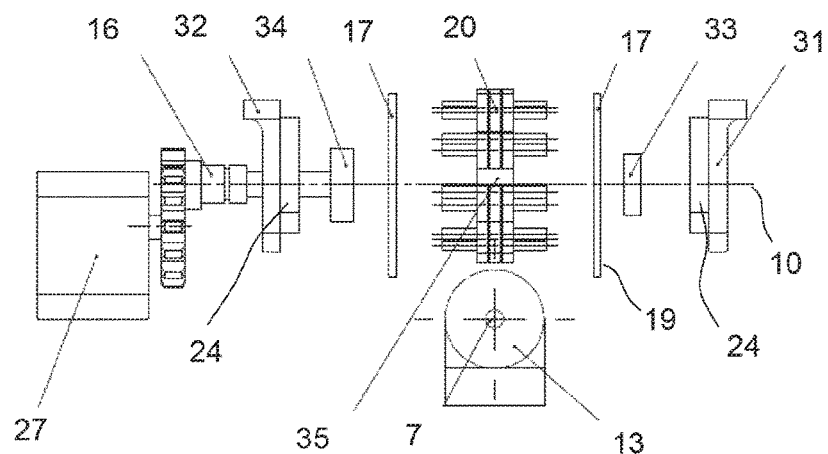
FIG. 6 shows an exploded view from the front of parts of the peristaltic pump of FIG. 1.
Figure 7:
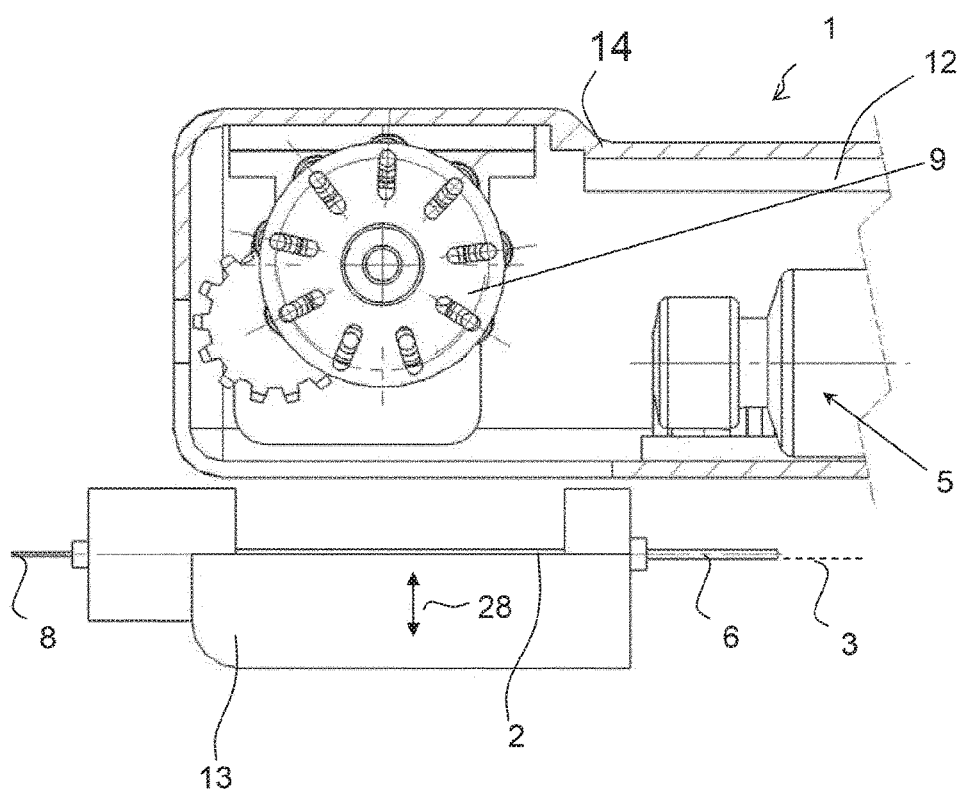
FIG. 7 shows a sectional side view of the peristaltic pump of FIG. 1 with an exchange part being detached from a main body.

Further details of an embodiment of the pump 1 of FIG. 1 can be seen from FIGS. 5, 6 and 7.

FIG. 5 shows a perspective exploded view of parts of the peristaltic pump 1 and FIG. 6 shows an exploded view from the front of parts of the pump 1.

As can be seen from FIGS. 5 and 6, the guide member 24 comprises a first part 29 and a second part 30, wherein the first part 29 guides the shafts 21 at one of their ends and the second part 30 guides the shafts 21 at their opposite ends. Each of the parts 29, 30 comprises a curved section 26 and a linear section 25. The first part 29 and the second part 30 are located on flanged members 31, 32, which are secured to a housing of the pump 1.

Furthermore, the pump 1 comprises an engine 27, which drives the pump head 9 via gears 16. Bearings 33, 34 are arranged at the discs 18, 19 of the support member 17 to facilitate a rotational movement of the support member 17.

Furthermore, a spacer ring 35 is arranged between the discs 18, 19 defining the distance between the discs 18, 19.

FIG. 7 shows the peristaltic pump 1 of FIG. 1, wherein the exchange part 13 has been removed from the main part 12. The exchange part 13 may be configured to be disposed after one or several operations of the pump 1 and replaced by a new exchange part 13. Alternatively, only parts of the exchange part 13 may be configured to be disposed, for example the needles 6, 8 or the tube 2.

The pump 1 may be configured such that for detaching and attaching the exchange part 13 from the main part 12, the exchange part 13 may have to be moved in directions 28 perpendicular to the longitudinal axis 3. In this case, it may be necessary to remove the cartridge or container 5 from the receptacle of the main part 12 before the exchange part 13 can be detached or attached to the main part 12, because otherwise an attachment may be blocked by an interaction of the needle 6 with the cartridge or container 5.

In a further embodiment, the pump 1 may be configured such that the exchange part 13 can be detached and attached by moving the exchange part 13 in a direction parallel to the longitudinal axis 3. In this case, it may not be necessary to remove the cartridge or container 5 from the main part 12 in order to detach or attach the exchange part 13. In particular, the first needle 6 may be inserted into the cartridge or container 5 during an attachment movement.

The invention claimed is:

1. A peristaltic pump, comprising:
a tube for transporting a material; and
a pump head rotatable about a rotation axis and configured to cause a squeezing of a portion of the tube, the portion of the tube to be squeezed being arranged linearly along a longitudinal axis, the pump head comprising at least one squeeze member for squeezing the tube and a support member rotatable about the rotation axis,
the support member including a slot for supporting the at least one squeeze member, the slot extending in a radial direction relative to the rotation axis throughout rotation of the support member about the rotation axis, and enabling movement of the at least one squeeze member in the radial direction.

2. The peristaltic pump of claim 1, wherein the portion of the tube to be squeezed is configured to be squeezed for transporting the material.

3. The peristaltic pump of claim 1, wherein the rotation axis is perpendicular to the longitudinal axis.

4. The peristaltic pump claim 1, wherein rotation of the at least one squeeze member relative to the support member is enabled.

5. The peristaltic pump of claim 1, further comprising a guide member for guiding a movement of the at least one squeeze member.

6. The peristaltic pump of claim 5, wherein the guide member is configured to guide a movement of the at least one squeeze member along the longitudinal axis.

7. The peristaltic pump of claim 5, wherein a perimeter of the guide member comprises a linear section extending parallel to the longitudinal axis.

8. The peristaltic pump of claim 1, wherein the at least one squeeze member includes a plurality of squeeze members.

9. The peristaltic pump of claim 1, comprising a main part and an exchange part configured to be detachable from the main part, wherein the exchange part comprises a tube guide for guiding the tube.

10. The peristaltic pump of claim 1, wherein the peristaltic pump is configured to transport a medicament.

11. The peristaltic pump of claim 1, wherein the at least one squeeze member is shiftable in the slot.

12. A peristaltic pump, comprising:
a tube for transporting a material, wherein at least a portion of the tube is arranged along a longitudinal axis;
a pump head configured to cause a squeezing of the tube, wherein the pump head is rotatable about a rotation axis, wherein the pump head comprises at least one squeeze member for squeezing the tube, and wherein the at least one squeeze member is shiftable in a radial direction relative to the rotation axis;
a non-rotatable guide member for guiding a movement of the at least one squeeze member; and
a tube guide for guiding the tube,
wherein the non-rotatable guide member is arranged relative to the tube guide such that a radial position of the at least one squeeze member relative to the rotation axis is confined in one radial direction by the non-rotatable guide member and in the opposite radial direction by the tube guide during a portion of the rotation of the pump head about the rotation axis, the confinement by the non-rotatable guide member and the tube guide during the portion of the rotation of the pump head about the rotation axis exerting forces on the at least one squeeze member to follow a linear path so as to enable squeezing of the tube.

13. The peristaltic pump of claim 12, wherein the portion of the tube arranged along the longitudinal axis includes a section of the tube configured to be squeezed for transporting the material.

14. The peristaltic pump of claim 12, wherein the rotation axis is perpendicular to the longitudinal axis.

15. The peristaltic pump of claim 12, wherein the pump head further comprises a support member for supporting the at least one squeeze member such that a rotation of the at least one squeeze member relative to the support member is enabled.

16. The peristaltic pump of claim 12, wherein the non-rotatable guide member is configured to guide a movement of the at least one squeeze member along the longitudinal axis.

17. The peristaltic pump of claim 12, wherein a perimeter of the non-rotatable guide member comprises a linear section extending parallel to the longitudinal axis.

18. The peristaltic pump of claim 12, wherein the at least one squeeze member includes a plurality of squeeze members.

19. The peristaltic pump of claim 12, comprising a main part and an exchange part configured to be detachable from the main part.

20. The peristaltic pump of claim 19, wherein the exchange part comprises the tube guide for guiding the tube.

21. The peristaltic pump of claim 12, wherein the peristaltic pump is configured to transport a medicament.

* * * * *

SEQUENCE LISTING

<160> NUMBER OF SEQ ID NOS: 1

<210> SEQ ID NO 1
<211> LENGTH: 39
<212> TYPE: PRT
<213> ORGANISM: Artificial Sequence
<220> FEATURE:
<223> OTHER INFORMATION: Synthetic

<400> SEQUENCE: 1

```
Ser Pro Pro Pro Ala Gly Ser Ser Pro Gly Gly Asn Lys Leu Trp Glu
1               5                   10                  15

Ile Phe Leu Arg Val Ala Glu Glu Glu Met Gln Lys Ser Leu Asp Ser
            20                  25                  30

Thr Phe Thr Gly Glu Gly His
            35
```